United States Patent [19]

Bennett, Jr.

[11] 4,226,245
[45] Oct. 7, 1980

[54] SYSTEM FOR DETECTING HEART PACEMAKER PULSES

[75] Inventor: Robert M. Bennett, Jr., Ham Lake, Minn.

[73] Assignee: Medtronic, Inc., Minneapolis, Minn.

[21] Appl. No.: 957,815

[22] Filed: Nov. 6, 1978

[51] Int. Cl.³ .............................................. A61N 1/36
[52] U.S. Cl. .............................................. 128/419 PT
[58] Field of Search .................. 128/419 PT, 697, 696

[56] References Cited

U.S. PATENT DOCUMENTS

| 3,498,288 | 3/1970 | Max et al. | 128/696 |
| 3,923,041 | 12/1975 | Stasz et al. | 128/419 PT |
| 3,986,496 | 10/1976 | Brastad | 128/419 PT |
| 4,087,637 | 5/1978 | Dekont | 128/697 |

OTHER PUBLICATIONS

Thomas et al., "Medical and Biological Engineering", vol. 9, No. 5, pp. 503–509, Sep. 1971.

Primary Examiner—William E. Kamm
Attorney, Agent, or Firm—R. Lewis Gable; Joseph F. Breimayer

[57] ABSTRACT

A system is disclosed for accurately providing a signal or signals indicative of the relatively sharp leading edge and the relatively attenuated trailing edge of a pulse and in particular of a pulse applied by a heart pacemaker to a patient's heart. The system of this invention functions to distinctly detect each of the relatively fast rising leading edge and the relatively slow rising trailing edge, while preventing a premature detection of the trailing upon the attenuated or drooping portion of the pacing pulse therebetween.

11 Claims, 19 Drawing Figures

SYSTEM FOR DETECTING HEART PACEMAKER PULSES

CROSS REFERENCE TO COPENDING APPLICATIONS

Attention is drawn to the following copending, commonly assigned applications, all filed on the same date and further describing the overall system in which the subject invention is incorporated:

"CARDIAC PACEMAKER HAVING A RATE LIMIT", by David L. Thompson, Ray S. McDonald, and Yan Sang Lee, Ser. No. 957,828, filed Nov. 6, 1978;

"DEMAND CARDIAC PACEMAKER HAVING REDUCED POLARITY DISPARITY" by Gerome P. Hartlaub and Ray S. McDonald, Ser. No. 957,812; filed Nov. 6, 1978;

"DIGITAL CARDIAC PACEMAKER" by David L. Thompson, Gerome P. Hartlaub, Ray S. McDonald, and Martin A. Rossing, Ser. No. 957,960, filed Nov. 6, 1978;

"FREQUENCY TO VOLTAGE CONVERTER FOR CARDIAC TELEMETRY SYSTEM" by Stanley L. Gruenenwald, Ser. No. 958,202, filed Nov. 6, 1978;

"PROGRAMMING AND MONITORING APPARATUS FOR A PROGRAMMABLE PACING GENERATOR" by Robert Smith, Ser. No. 958,063 (now indicated to be allowed), filed Nov. 6, 1978.

BACKGROUND OF THE INVENTION

1. Field of the Invention

This invention relates to systems for detecting the occurrence of the leading and trailing edges of pulses and in particular of those pulse-like signals applied by a pacemaker to a patient's heart.

2. Description of the Prior Art

Heart pacemakers such as that described in U.S. Pat. No. 3,057,356, issued in the name of Wilson Greatbatch and assigned to the assignee of this invention, are known for providing electrical stimulating pulses to a patient's heart whereby it is contracted at a desired rate in the order of 72 beats per minute. A heart pacemaker is capable of being implanted in the human body and operative in such an environment for relatively long periods of time, to provide cardiac stimulation at relatively low power levels by utilizing a small, completely implanted, transistorized, battery-operated pacemaker connected via flexible electrode wires directly to the myocardium or heart muscle. The electrical stimulating pulses by this pacemaker are provided at a relatively fixed rate.

Typically, such heart pacemakers are encapsulated in a substance substantially inert to body fluids, and are implanted within the patient's body by a surgical procedure wherein an incision is made in the chest beneath the patient's skin and above the pectoral muscles or in the abdominal region, and a pacemaker is implanted therein. Due to the inconvenience, expense and relative risk to the patient's health, it is highly desired to extend the life of the power source or battery, whereby the number of such surgical procedures is limited. The resultant problem for the attendant doctor is to determine when the batteries should be replaced, keeping in mind the relative risk or probability of premature pacer failure due to battery depletion.

After surgical implantation of an artificial heart pacemaker by known surgical techniques, the patient is required to have periodic checkups so that the heart pacemaker function may be monitored for possible battery or other failure.

A major problem with these devices is that battery failure is not precisely predictable statistically and while statistics do exist they are unfortunately gathered after pacemaker failure has occurred. Further, present heart pacemakers available have a functional life expectancy of about two to five years, but individual ones may not exceed this, and in fact may rather unpredictably fail before this statistical determined period. Usually approximately 90 percent of heart pacemaker failures are battery failures, and the remaining 10 percent are a result of other types of failures, the next most common failure being in the leads themselves. Electronic component failure in artificial cardiac pacers is generally a very small factor. However, all of these factors must be considered when diagnosing a possible malfunction.

The number and kinds of variables that exist make an accurate a priori prediction of the lifetime of a given heart pacemaker difficult. The problem therefore is that of measuring the heart pacemaker pulse, the interval between impulses and some characteristics or set of characteristics which will allow determination in advance of a critical situation, i.e., when the heart pacemaker is about to fail.

One such characteristic is that as the battery starts to fail, the voltage output of the pulses starts to drop and generally as the voltage drops the width of the pacemaker pulse changes. Further, in most heart pacemakers the rate of firing changes.

Most pacemakers generally are powered by 4 or 5 miniature batteries. Present monitoring techniques are geared to detect when the first of those 5 batteries has failed, which means that the safety factor is decreased. In any event, a failure of not only one cell but generally two can be tolerated before the patient is in any danger. It should be cautioned however that when a battery does fail, it fails very rapidly. The battery voltage remains almost constant throughout the lifetime of the battery. Therefore, changes may be detected in the pacemaker output pulses by comparing measurements from one checkup to another.

In one approach to the problem of accurately determining battery depletion, pacemakers such as described in U.S Pat. No. 3,842,844 are provided with a battery or cell depletion indicator that increases the pulse width of the output signal as their batteries deplete, i.e., their voltage amplitude decreases. Further, as the power source or battery depletes, the pulse repetition rate of such artificial cardiac pacemakers also decreases. For example, at the time of implantation, a heart pacemaker may produce stimulating pulses at 70 beats per minute (BPM), plus or minus two beats, with a pulse width in the order of 0.5 msec. After a period of service illustratively in the order of 2-4 years, the BPM changes in the order of 5-10%, i.e., a decrease of 5-7 beats from the original BPM, and the pulse width may increase to a value in the order of 1 msec. Dependent upon the known histories of such batteries, such a change in the BPM as well as a change in pulse width indicates that one of a plurality (e.g. 4 or 5) cells has failed, and that it is time to replace the batteries within the implanted pacemaker to assure continued heart stimulation of a sufficient level.

Pulse width increase is desired to order that as the amplitude of the voltage provided from the pacemaker battery decreases, the total energy in the stimulating pulse remains substantially constant. It is understood that the voltage level of the pacemaker battery may decrease below a level at which the heart may not respond regardless of the pulse width. Further, as the pulse width increases to compensate for decreases in the voltage level, the current drain upon the battery increases, thereby increasing the rate of battery depletion.

In order to detect the patient's electrical heart activity, electrodes are attached for example to the patient's body including his right arm, left arm, left leg, chest and right leg. The electrical activity, as shown in FIG. 2, includes the patient's ECG signal upon which is impressed the pacer pulse appearing before the QRS wave form, which is generated naturally by the heart's activity. The pacer pulse is usually of large amplitude and very small width. Though noting that it is desired to measure the width of the pacer pulse, it is very difficult to determine the width with accuracy. Conventional monitors, for example, do not have a sufficient band width to pass the pacer pulse with any reasonable degree of fidelity. Further, it is necessary to distinguish the pacer pulse from the patient's QRS wave, as well as 60 cycle noise and muscle artifacts. One of the distinguishing characteristics of the pacer pulse is that it has a very fast rise time, being typically in the microsecond range. By contrast, the electrical impulses normally originated in the heart or other noise sources such as 60 Hz line noise, have rise times in the order of 10-20 milliseconds. Other common noise sources may be generated by electrical appliances being operated from the same power line. These generally have fast rise times but very short duration. Since these individual pulses generally are only of fractions of microseconds long, they are distinguished from heart pacemaker pulses principally by the pulse widths since heart pacemaker pulses are commonly in the 1 millisecond range. Thus, the heart pacemaker pulses may be identified by their relatively fast time and their relatively long pulse width in the order of 0.5-4 milliseconds.

In U.S. Pat. No. 3,885,552 of Kennedy, there is disclosed a cardiac monitoring system for monitoring the heart activity and in particular for measuring among other parameters the width of the heart pacemaker pulses. In particular, there is disclosed a pacer pulse selection logic circuit including a differentiator having a time constant of approximately 100 microseconds for providing an output if the applied input has a rise time shorter than 100 microseconds. Further, the noted logic circuit also includes an integrator circuit providing a signal going low indicating that the pulse width of the applied signal is greater than a selected minimum pulse width of 250 microseconds. The Kennedy circuit functions to provide an output identifying the presence of a pacer pulse upon the occurrence of both a signal from the aforementioned differentiator and integrating circuits. For a similar disclosure of a system for detecting the presence of a pacer pulse, attention is also drawn to U.S. Pat. No. 3,871,363 of Day which similarly discloses the use of a differentiator circuit and an integrator circuit for respectively measuring rise times smaller than a selected minimum and pulse widths in excess of a predetermined width to identify thereby heart pacemaker pulses.

Reference is made to FIG. 5, which generally shows an implanted pacemaker of the type generally described above having an output capacitor C3 that is coupled by suitable electrodes to the patient's heart, which for the sake of simplicity may be considered as presenting an essentially resistive impedance to the output of the heart pacemaker. In typical operation, the pacemaker generates a series of timing pulses applied to the base of transistor Q thereby rendering this transistor Q conductive and "dumping" the charge established upon capacitor C3 across the heart's resistance R2. It is recognized, that such a circuit is essentially a differentiation circuit, whereby the electrical signal discharged across the resistor R2 has an essentially sloping or curved waveform as indicated in FIG. 4A. As shown in FIG. 4A, the pulse appearing between times t1 and t2 has a very fast rise time beginning at time t1, generally sloping down to time t2 with the fast fall time at that instant; this pulse has relatively sharp, well defined leading and trailing edges making its detection relatively easy. However, in practice, the detected wave shape of a pacemaker pulse is more as shown in the time interval between t3 and t5, of FIG. 4A. Generally, the differentiation process effected by the output capacitor C3 and the heart's resistance R3 accounts for the relatively poor wave shape quality, i.e., attenuated quality of this pulse. Thus, it may be observed that the leading edge is relatively well defined and thus may be accurately detected. On the other hand, the trailing edge is of a degraded wave form making its detection more difficult. Thus, it is difficult to accurately detect and measure the pulse width of such a heart pacemaker pulse.

In the above-noted prior circuits for detecting pulse widths, a differentiator circuit is used to detect the leading and trailing edges. Typically, there is no problem in detecting the occurrence of the leading edge of a pacer pulse, which under normal circumstances has a sufficiently fast rise time to actuate normal differentiator circuits to provide a defined output pulse. Similarly, prior art differentiator circuits are capable of providing an output corresponding to the trailing edge, even of a degraded pulse as shown in FIG. 4A. The problem then arises when the attenuated or degraded slope of the pulse occurring between the leading and trailing edges may have a sufficiently fast fall time such that the output of the differentiator circuit may have a sufficient amplitude so as to cause the associated threshold circuit to provide a premature output indicative of the trailing edge. As shown in FIG. 4A, the drooping waveform portion of the pacemaker pulse is essentially capacitive in nature being attenuated by the indicated expression. Therefore, the droop or attenuation associated with the detected artifact pulse is predictable, assuming that a reasonable range of capacitive coupling is made to the patient's heart. The worst contemplated case of attenuation is considered to be a decrease in impulse amplitude of 50% within a time period of 200 microseconds or 80% in 1 millisecond. In other words, the leading edge of a degraded pulse may have a time constant in the order of 3 or 4 microseconds, the trailing edge a time constant in the order of 70 microseconds, and the attenuated or drooping intermediate waveform portion may have a time constant in the order 620 microseconds. Though many multiples of either the leading or trailing edge, the time constant of the drooping portion may be sufficient to provide a premature indication of the trailing edge and therefore an incorrect indication of the pulse width.

SUMMARY OF THE INVENTION

The system of this invention functions to detect the leading and trailing edges of an electrical pulse and in particular of a pulse applied by a heart pacemaker to a patient's heart. The system of this invention functions to distinctly detect each of the relatively fast rising leading edge and the relatively slow rising trailing edge, while preventing a premature detection of the trailing upon the attenuated or drooping portion of the pacing pulse therebetween. The patient's heart activity signals comprising the pacing pulse is applied along with extraneous noise including the patient's QRS wave, 60 Hz noise, muscle artifacts, etc., are applied to a differentiator or wave shaping amplifier whose gain or transfer function is configured to reject signals having low frequency components, i.e., the noise signals mentioned above. The output of the differentiator is applied to a first input of a differential amplifier, while the aforementioned heart activity signals are applied to a second input; the differential amplifier circuit essentially subtracts the amplifier output from the heart activity signals to remove the DC component from the output of the amplifier circuit. If the amplifier output is above a predetermined amplitude, the differential amplifier output is applied to a first threshold circuit or leading edge detector to provide an output signal indicative of the occurrence of the leading edge, and to set a one shot circuit, which in turn provides a signal initiating the detection of the trailing edge. The output of the wave shaping amplifier is also applied via a limiter or amplifier to a second threshold circuit, which responds to signals above a predetermined threshold to provide a signal indicative of the occurrence of the trailing edge. Noting that the output of the waveshaping amplifier is less to the trailing edge than the leading edge, the gain of the amplifier, as well as the time constant of the waveshaping amplifier and the threshold level of the second threshold detector is set to detect the trailing edge of the pacemaker pulse. The output of the first threshold circuit corresponding to the leading edge and the output of the second threshold circuit corresponding to the trailing edge are applied to a logical circuit to provide a defined output pulse whose leading and trailing edges sharply define the leading and trailing edges of the pacer pulse and therefore the pulse width therebetween.

In an illustrative embodiment of this invention, the pulse width detection circuit is incorporated into a low bandwidth transmission system, wherein the heart activity of the patient is transmitted over a low band width transmission medium, e.g., a telephone line, to a remote station as in a physician's office whereat the physician may observe not only the pulse width of the cardiac pulse but also the heart's ECG signal. At the transmitter of such a system, the ECG signals are amplified and applied to a voltage controlled oscillator (VCO) to provide an audio output signal of a frequency dependent upon the amplitude of the input voltage. The heart activity signal is also applied to the aforementioned pulse width detection circuit whereby the pulse width of the pacemaker pulse is accurately detected and subsequently stretched by a given factor to cause the aforementioned VCO to oscillate at a predetermined frequency. Thus, a signal corresponding to the ECG of the patient's heart and a signal indicative of the pulse width of the pacer pulse, i.e., the signal of predetermined frequency, are transmitted via a transducer and the low bandwidth transmission medium to the remote station, where they are detected and appropriately displayed.

BRIEF DESCRIPTION OF THE DRAWINGS

The advantages of the present invention will become more apparent by referring to the following detailed description and accompanying drawings, in which.

DESCRIPTION OF THE PREFERRED EMBODIMENT

Figure 1A:
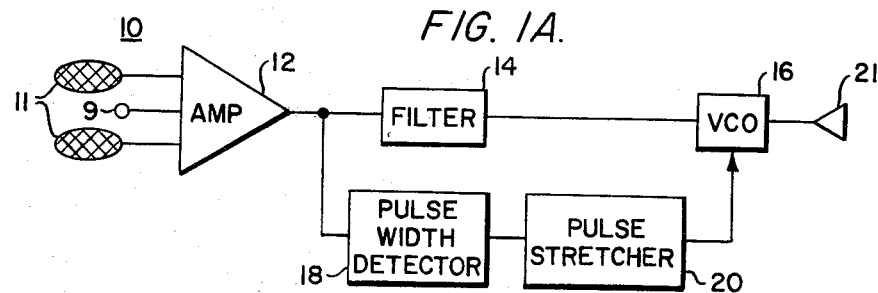
FIG. 1A is a functional block diagram showing a transmitter for detecting and transmitting heart activity signals via a low bandwidth transmission medium to a receiver, as shown in FIG. 1B.
Figure 1B:
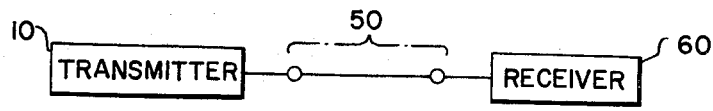

Referring now to the drawings and in particular to FIG. 1B, there is shown a simplified diagram illustrating the relationship of a transmitter 10 for detecting and transmitting the electrical activity of the patient's heart, e.g., the patient's electrocardiogram (ECG) upon which has been superimposed the detected stimulating pulse in accordance with the teachings of this invention, across a relatively low bandwidth transmission medium 50 to be received by a receiver 60, which operates to separate the multipled or stretched stimulating pulse and to display it with significant accuracy, whereby the attending physician can determine accurately the width of the stimulating pulse and the state of the pacemaker's energy source. It is evident that the transmitter 10 may be a relatively portable unit that is adapted to be coupled to a telephone set, whereby the desired signals are transmitted over the telephone lines or transmission medium 50. At the end of the transmission medium 50, the receiver 60 is adapted to be coupled to another telephone set, whereby the transmitted signal may be converted to electrical signals within the receiver 60 to be processed and displayed as to be described in more detail.

In FIG. 1A, there is shown a simplified schematic of the transmitter 10, shown in block form in FIG. 1B. In particular, a pair of electrodes 11 is attached to the patient, as upon the inside of his forearms or legs, whereby the electrical activity of the patient's heart and the stimulating pulse as generated and applied to the patient by the implanted heart pacemaker, are detected and applied to an amplifier 12. The detected signal is amplified by the amplifier 12 before being applied to the EKG channel comprised of a filter 14 and a voltage controlled oscillator 18. The filter 14 serves to block the pacemaker stimulating pulses from the ECG channel. Further, the amplified signal is also applied to a pulse width detector 18 in accordance with the teachings of this invention, for providing an output sharply defining the pacer pulse width, and a pulse stretcher 20 whereby the detected pulse is stretched by a fixed factor, dependent upon the carrier signal to be transmitted along the transmission medium 50 to a display, e.g., a strip recorder, within the receiver 60, whereby the pulse width as displayed thereon does not mask other information of interest to the patient's doctor. Illustratively, the factor is selected to be within the range of 30–50 with a preferred value being in the order of 40. By selecting a multiplication factor in the noted range, the superimposed, multiplied pulse is of sufficient duration with respect to the frequency of the carrier signal, that no significant amount of the width of the stimulating pulse is lost. At the same time, even with a factor of 50, a pulse of normal width, e.g., 1.0 msec, as received and displayed by the receiver 60 does not unduly mask the other information as displayed at the remote station. The transmitter and receiver as generally shown in FIGS. 1A and 1B are more specifically described in U.S. Pat. No. 3,986,496 of Brastad, which is assigned to the assignee of this invention.

Figure 2:
FIG. 2 is a graph showing a patient's ECG signal upon which there has been imposed pacer pulse signals.
Figure 5:
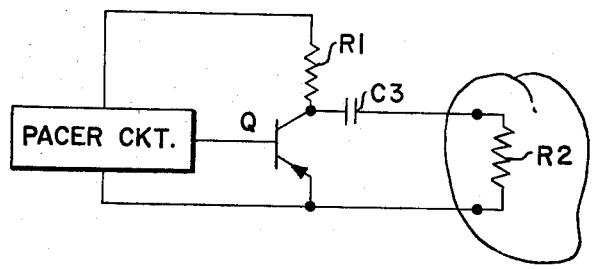
FIG. 5 is a functional block diagram of the circuit formed by the output of a heart pacemaker and the patient's heart.

It is contemplated that in accordance with the teachings of this invention, that the pulse width of the pacer pulse may be accurately detected and then transmitted to the remote station at the physician's office where the physician or a trained technician may accurately observe the patient's heart activity as shown in FIG. 2. In FIG. 2 of the drawings, there is shown a typical graph of the electrical activity of a patient's heart which is stimulated by pulses derived from an artificial heart pacemaker. The heart activity or electrocardiogram (ECG) of the patient is indicated in FIG. 2 by the letter "B," whereas the stimulating pulse is identified by the letter "A," whose pulse width is indicated with the letters "PW." Noting that the threshold for stimulation of the heart varies from patient to patient, the minimum pulse width of the stimulating pulse is in the order of 100 μsec and its minimum voltage amplitude is in the order of 0.5 V. Typically, the amplitude of the stimulating pulse would be in the order of 6 V.

Figure 3:
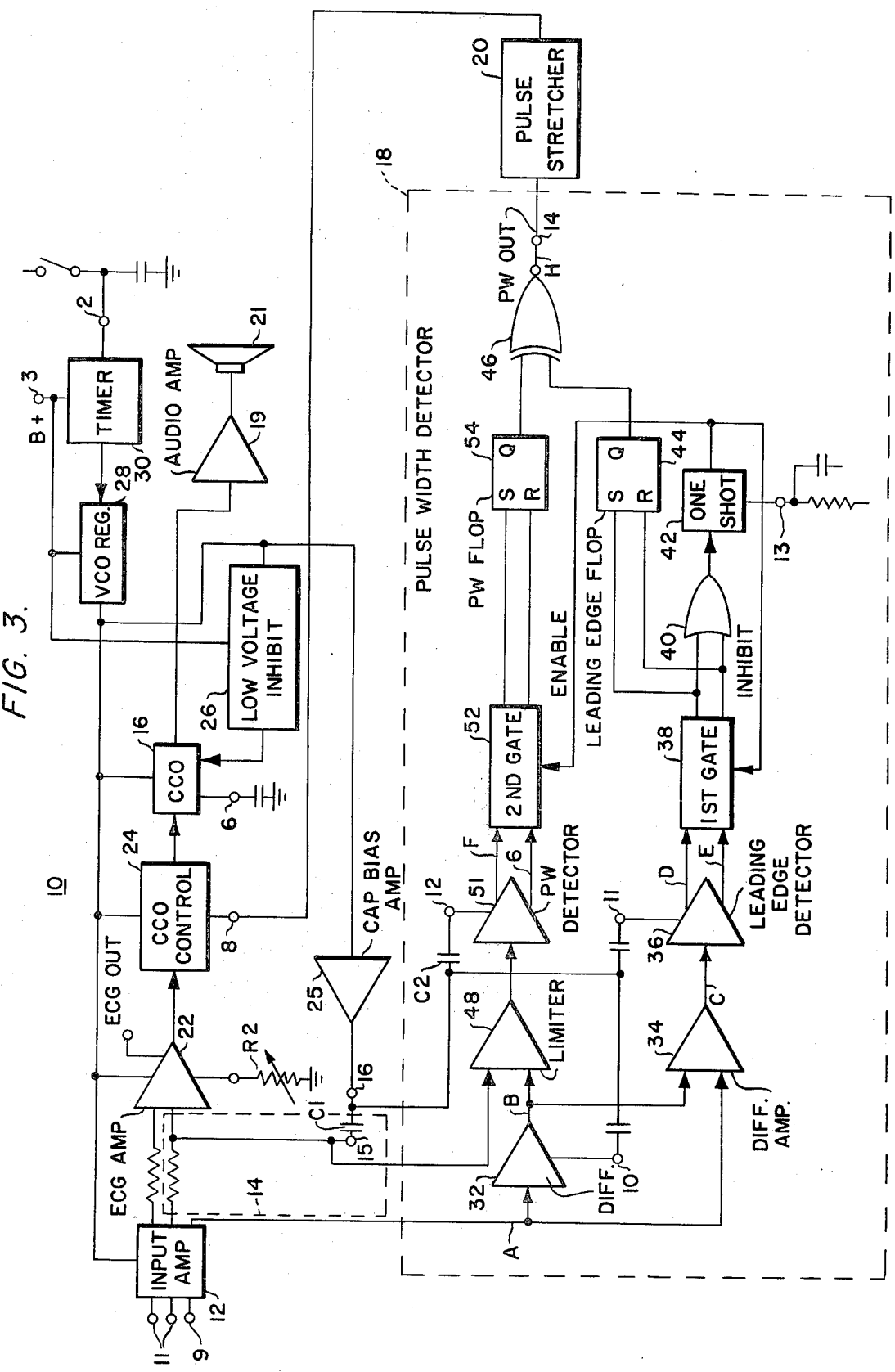
FIG. 3 is a functional block diagram of the transmitter particularly illustrating the pulse width detector in accordance with the teachings of this invention.

Referring now to FIG. 3, there is shown an illustrative embodiment of the transmitter 10 generally shown in FIG. 1A and in particular an illustrative embodiment of the pulse width detector 18 in accordance with the teachings of this invention. The patient's ECG signals and the pacemaker pulse or artifact signals are sensed by a pair of electrodes 11 worn on the patient's arms and if utilized, an electrode 9 worn on the patient's right leg (or other location of the body) and applied to an input amplifier 12. The input amplifier 12 amplifies the input signals rejecting errors caused by common mode signals of large amplitudes that may be present. In a normal amplifier such common mode signals would tend to mask out the desired low level ECG and pacemaker pulse signals and even cause amplifier malfunctions such as saturation. The input amplifier 12 has a high input impedance, a low output impedance and typically greater than unity gain, for example, a gain of 2. The high input impedance is required because of the high source impedance which can occur between the electrodes 11 and the patient's skin. The signals via the electrode 9 are driven by an amplifier (not shown) that provides a sense common mode voltage to the input amplifier 12. Such a system is well known in the art and may take the form of a Hewlett-Packard driver lead EGC system. The input amplifier 12 provides a buffered, single ended output to the following signal processing circuit now to be described.

As apparent from FIG. 3, the buffered outputs are applied to the pulse width detector 18 wherein the pacemaker pulse or artifact signals are detected and whose pulse width is accurately determined, as well as to circuitry for amplifying and processing the ECG signals, now to be described. In particular the output of the input amplifier 12 is applied to an ECG amplifier 22 that converts the ECG wave form to current and provides a sufficient gain to realize the desired sensitivity of the current control oscillator 16. The gain of the ECG amplifier 22 is controlled by the setting of the potentiometer R2. The amplified ECG signal is applied to a CCO control circuit 24 that controls the mode of operation of the CCO. As seen in FIG. 3, an input is received from the pulse stretcher 20, which upon being rendered high, causes the CCO 16 to provide an output of selected frequency, e.g., 2250 Hz, for a period of time corresponding to the multiplied or stretched pulse width of the pacemaker pulse. The output of the CCO control circuit 24 is applied to the current control oscillator 16 which modulates the frequency of its output in accordance with the amplitude of the input current signal to provide an output that is amplified by an audio amplifier 19 to drive a transducer 21 in the form of a speaker. It is contemplated as shown in FIG. 1B, that the transducer 21 would be coupled to a telephone receiver, whereby the audio signals derived from the transducer 21 are reconverted to electrical signals to be transmitted over the medium 50 to the receiver 60. Further, there is included a timer 30 which automatically disconnects the power voltage as derived from a voltage regulator 28 from the remaining portions of the system to thereby terminate transmission of the patient's heart signals after a time sufficient to provide the physician an adequate sample thereof. Typically, this may be in the order of about 30 seconds. Further, there is included a low voltage inhibit circuit 26, which senses the power source potential to thereby disable the current control oscillator 16 when the voltage level of the power source falls below a desired level. In this regard, it is contemplated that the transmitter 10 may be a portable unit powered by a power source such as a battery. A capacitor bias amplifier 25 is coupled to the $V_{CC}$ regulator 28 to keep the voltage disposed across the capacitor C1 of the filter 14, which capacitor C1 is the low frequency cut off the ECG amplifier 22, as low as possible to avoid leakage effects from causing errors in the frequency of the output of the CCO 16. Further, the capacitor bias amplifier 25 also supplies a node that follows the voltage $V_{CC}$ as derived from the regulator 28 so that capacitors may be tied to it instead of ground, thereby to avoid inducing supply related transients across these capacitors.

Figure 4A:
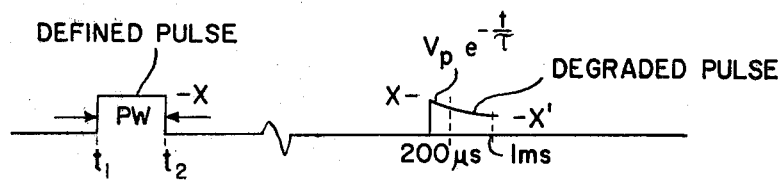
FIGS. 4A-4H show the wave forms of various signals as imposed upon the pulse width detector of FIG. 3.
Figure 4B:
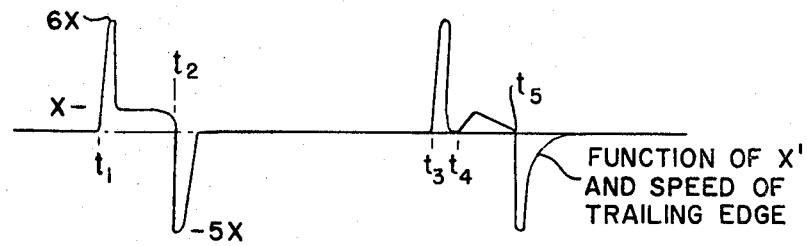
Figure 4C:
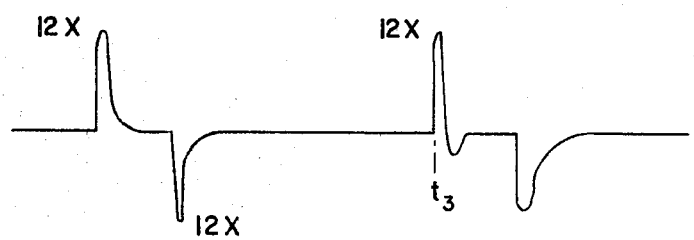

As shown in FIGS. 1A and 3, the heart signals are applied from the input amplifier 12 also to the pulse width detector 18 and in particular to a differential amplifier circuit 34 to provide an output as seen in FIG. 4C. In this regard it is understood that the pacemaker pulse or artifact signal as derived from the input amplifier 12 generally resembles those as shown in FIG. 4A. It would be desired to have a well defined pacer pulse as shown in the time period from t1 to t2, but as explained above its wave shape is often degraded to appear as shown by that pulse appearing in FIG. 4A between times t3 and t5. The artifact signals are also applied to a wave shaping amplifier or differentiator circuit 32, whose output is shown in FIG. 4B. More specifically, the differentiator 32 responds to the leading edge appearing at either times t1 or t3 to provide a sharply rising spike on the positive going edge of the pacer pulse. The positive going spike is followed by a shelf which corresponds to the DC amplitude of the input pacer pulse as shown in FIG. 4A. It is noted that the amplitude X will vary from patient to patient, dependent upon the level of stimulation by the implanted pacemaker, as well as the efficiency of the electrical connection between the patient's body and input amplifier 12. At time t2 the differentiator circuit 32 provides a negative going spike corresponding to the trailing edge of the input pulse appearing at times t2 and t5. In the time period t3 to t5, a poor quality pacemaker pulse is sensed which may have a drop or fall of 80% within one millisecond. The differential amplifier 32 processes such an input pulse and provides an output as shown in FIG. 4B between the time period t3 and t4. It is noted that at t4, the wave form of FIG. 4B falls to a point slightly below the reference level and then resumes a shelf to time t5 at which time there is provided a negative going spike.

The heart activity signals including the pacing pulses are also applied to a first input of a differential amplifier circuit 34, while the output of the differentiator 32 is applied to a second input of the differential amplifier 34. Essentially, the differential amplifier 34 amplifies the difference of these two signals, thus removing the DC level component as shown in FIG. 4B of the differentiator output, to provide an output as shown in FIG. 4C. The amplifier output including a first spiked signal indicative of the leading edge of the pacing pulse and a second spiked signal indicative of the trailing edge of the pacer pulse, is applied to a leading edge detector or first threshold level circuit 36, which provides an output upon its line D when the first spiked signal appearing at t1 is positive going and exceeds a predetermined positive level, and an output upon its E line when the first spiked signal is negative going and exceeds a negative, similar level.

Figure 4D:
Figure 4E:
Figure 4F:
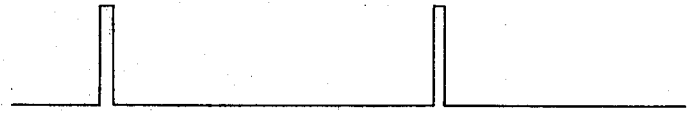
Figure 4G:

It is noted that the input pacemaker pulses may be either negative or positive going; therefore the leading edge detector 36 is capable of detecting negative and positive going spikes of a similar predetermined level. The outputs on the D and E lines are applied to a gate 38 that is normally enabled to pass these signals to an OR gate 40 to set a one shot multiplier 42, and to a leading edge flip-flop 44 to set the flip-flop 44 if a positive going leading edge is detected and to reset the flip-flop 44 if a negative leading edge is detected. The outputs of the leading edge detector 36 are respectively shown in FIGS. 4D and 4E.

As shown in FIG. 3, the output of the one shot multiplier 42 is also applied to enable a second, normally disabled gate 52 to initiate the detection and processing of the second spiked signal corresponding to the trailing edge of the pacemaker pulse. The output of the differentiator circuit 32, as shown in FIG. 4B, is applied to a limiter circuit or amplifier 48, which functions to amplify this input with a selective gain and to apply the amplified wave forms similar to that shown in FIG. 4B to a pulse width detector or second threshold circuit 51. The pulse width detector 51 detects positive and negative going trailing edges to provide upon its output lines F and G, respectively, signals if the amplitude of the input spikes exceed a predetermined level.

In operation, a pacemaker pulse as shown in FIG. 4A is applied to each of the first and second differential circuits 34 and 32 respectively. Considering first the detection of the leading edge as occurs at time t3, the differentiator circuit 32 provides an output as shown in FIG. 4B that is applied along with the pacemaker pulse to the inputs of the differential amplifier circuit 34 to provide an output as shown in FIG. 4C. The differential circuit 34 in a sense removes the DC component notably the shelf between the positive and negative going spikes to provide an output as shown in FIG. 4C. If as shown in FIG. 4C, the initial spiked signal is positive going, the leading edge detector 36 provides an output signal upon its D line if the amplitude of the positive going spike is above its threshold level. Assuming so, the signal on the D line is passed by the first gate 38 and applied via the OR gate 40 to set the one shot multiplier 42, thereby inhibiting the first gate 38 and enabling the second gate 52. At the same time, the output of the first gate 38 is applied to set the leading edge flip-flop 44 whereby its Q output goes high. Conversely, it may be understood that if the leading edge of the pacemaker pulse and therefore the initial spiked signal as derived from the differential amplifier 34 is negative going, an output is provided on the E line and applied to reset the leading edge flip-flop 44, driving its Q output negative.

At a point in time between t3 and t5, the second gate is been enabled, permitting the passage of signals to a pulse width flip-flop 54. Assuming that the output of the second differentiator circuit 32 is as shown in FIG. 4B, i.e., the trailing edge is a negative going signal, that negative signal is amplified by the limiter 48 and applied to the pulse width detector 51, whereby if the amplitude of the negative going spike is above the threshold level of the pulse width detector 51, an output is developed upon its G line and applied via the enabled second gate 52 to reset the pulse width flip-flop 54, thereby driving its Q output negative. Thus, it is seen that at the time t3 when a positive going spike appears, a high signal is applied from the flip-flops 44 and 54 to the inputs of the exclusive NOR gate 46, which then provides a high output. When as in the example discussed above, the trailing edge is evidenced by the negative going spike of FIG. 4B at time t5, the flip-flop 54 is reset driving the exclusive NOR gate 46 low. Thus, the NOR gate 46 provides a sharply defined output as shown in FIG. 4H going high at time t3 and going low at time t5, thereby defining the leading and trailing edges of the pacemaker pulse.

Figure 4H:

As shown in FIGS. 1A and 3, the output pulses of FIG. 4H are applied from the exclusive NOR gate 46 to the pulse stretcher 20 to be multiplied or stretched by a given factor before being applied to the CCO controller 24, whereby the current control oscillator 16 is disposed into its mode of operation where it generates a signal of fixed frequency for a period corresponding to the pulse width of the pacemaker pulse. As indicated above, with respect to FIG. 1B, this signal may be transmitted via the transmission medium 50 to a receiver 60, whereat it is detected and suitably displayed for the benefit of the physician or his technician.

Figure 6A:
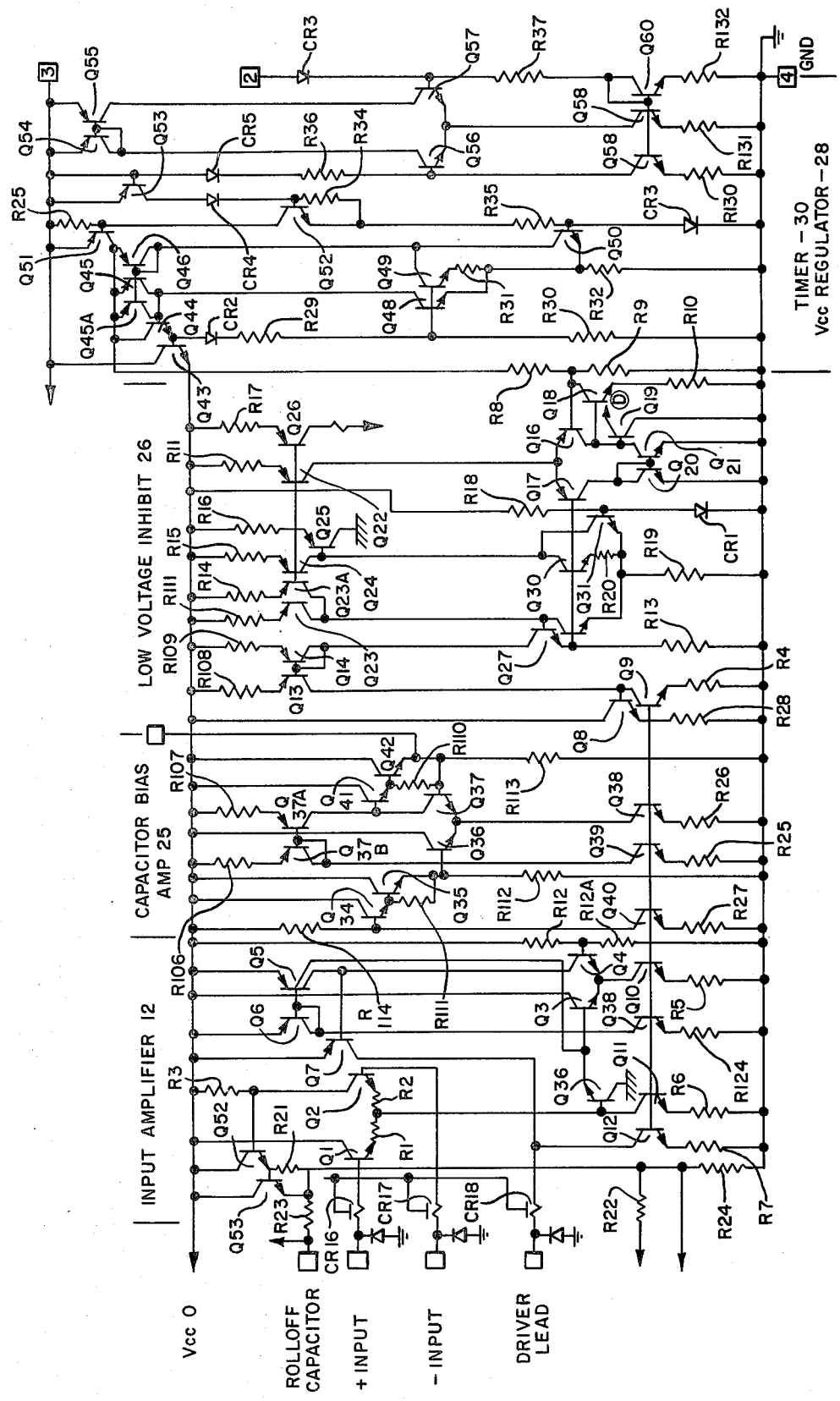
FIGS. 6A, B and C are detailed circuit diagrams of the transmitter and pulse width detector as more generally shown in FIG. 3.
Figure 6B:
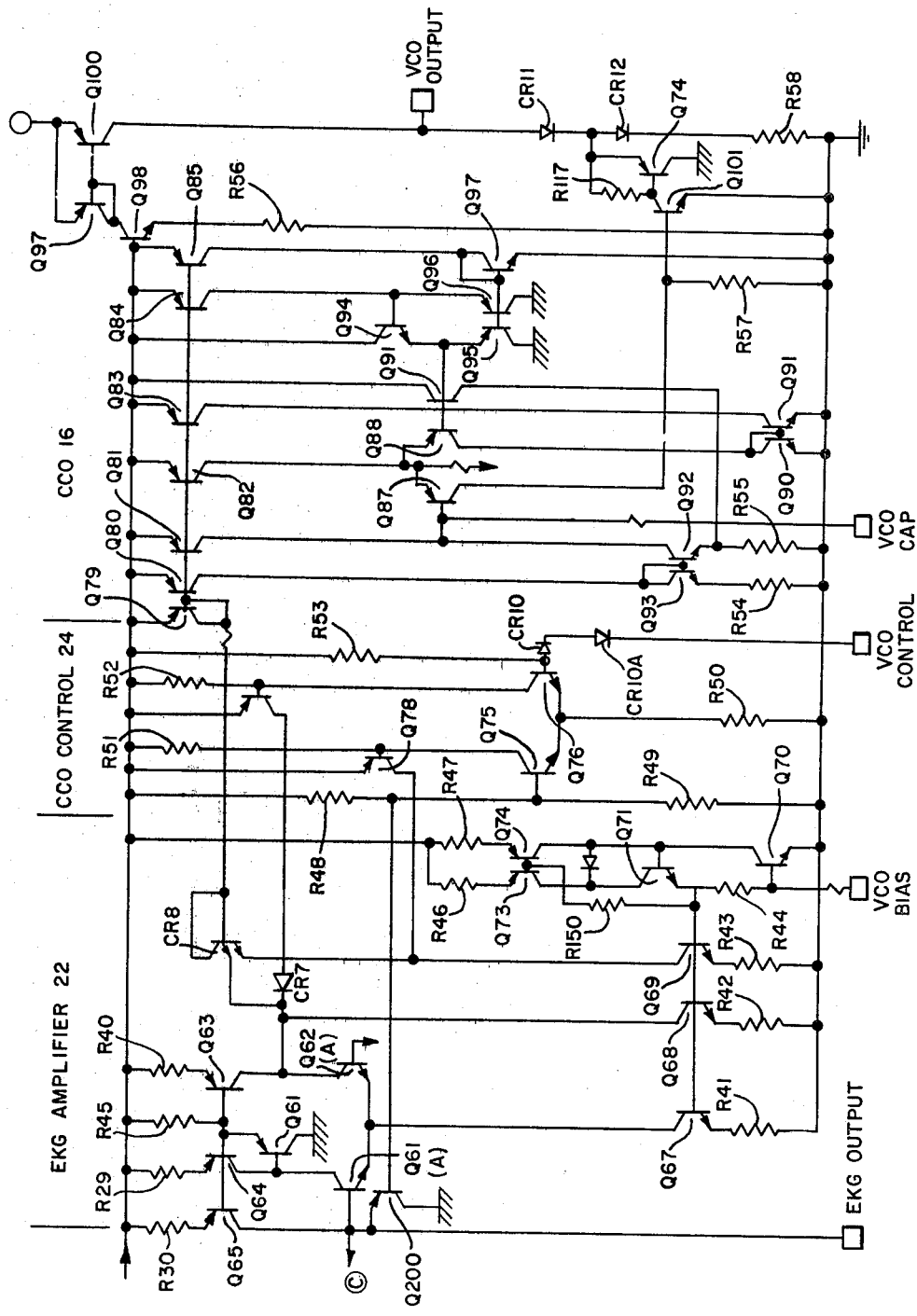
Figure 6C:
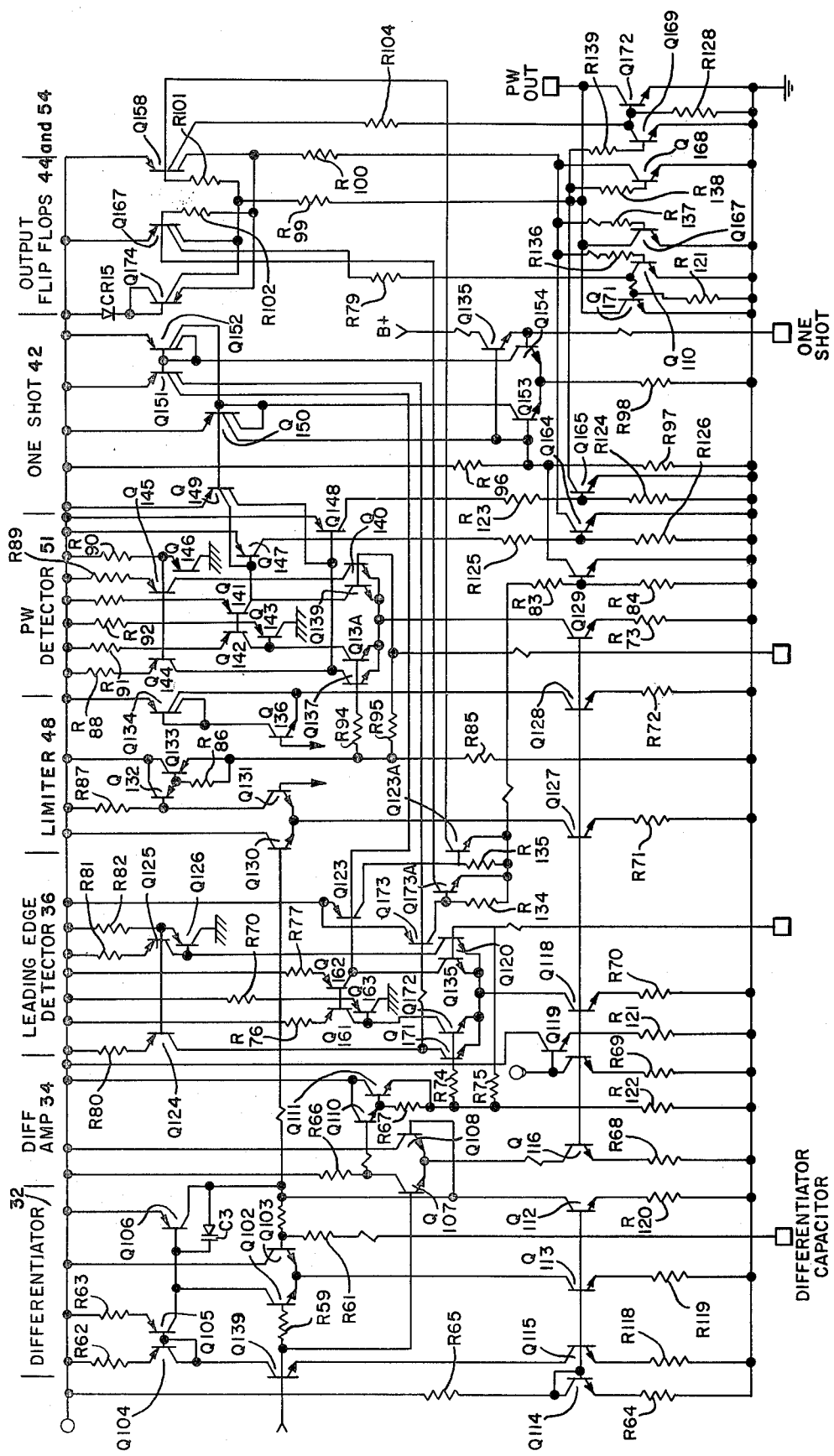

Referring now to FIGS. 6A, B and C, there is shown detailed drawings of the circuit elements making up the block diagrams more generally shown in FIG. 3. Each of the block diagrams shown in FIG. 3 will now be discussed below with regard to FIGS. 6A, 6B and 6C.

Figure 7:
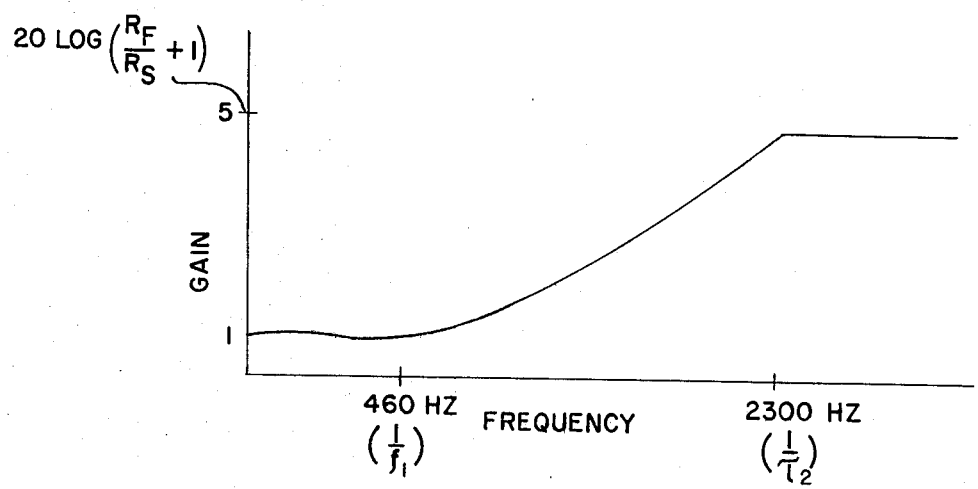
FIG. 7 is a graph showing the transfer function or graph of the wave shaping amplifier or differentiator of FIGS. 3 and 6C.
Figure 8A:
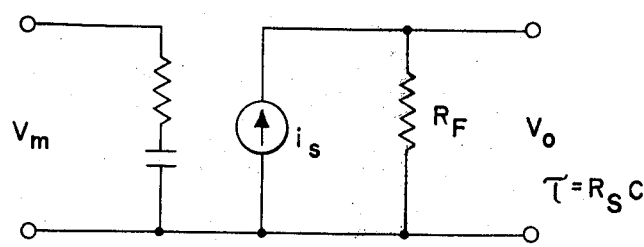
FIGS. 8A and 8B show respectively a theoretical model of electrical operation of the wave shaping amplifier, and the desired and undesired responses of such an amplifier.
Figure 8B:
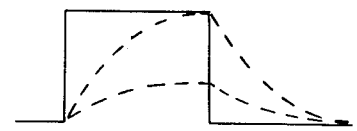

A significant aspect of this invention resides in accurately detecting an attenuated pacer pulse as seen in FIG. 4A by separately sensing and processing the leading and trailing edges of the pulse, while taking particular precautions not to sense the droop or attenuated waveform portion of the pulse between the leading and trailing edges, which otherwise might provide a false, premature indication of the trailing edge. To this end, the characteristics and parameters of the elements of the pulse width detector 18 and in particular the differential amplifier 34, the differentiator or wave shaping amplifier 32, the limiter or amplifier 48, and the threshold detectors 36 and 51 are critically selected. As shown in FIG. 3, the heart activity signals including the pacer pulse signal of interest, as well as noise including 60 Hz signals, power line interference and muscle artifacts are applied to the input of the differentiator circuit 32 as well as to one input of the differential amplifier 34. As a study of the specific circuitry of the differentiator 32 in FIG. 6, to be discussed, will indicate, the differentiator 32 is not a conventional differentiator. In a sense, the circuit 32 is considered to be a pseudo-differentiator in that its output as shown in FIG. 4B resembles the expected output of a differentiator, but in a more critical sense, as will now be explained, circuit 32 is a wave shaping amplifier processing its input in accordance with a selected transfer function, that is designed to condition the artifact pulse to permit accurate detection of its leading and trailing edges and in particular to prevent a response to the attenuated or drooping waveform portion of the detected pacer pulse, which might otherwise provide a false, premature indication of the trailing edge. As shown in FIG. 7, the transfer or gain function of the circuit 32, i.e., a graph plotted in terms of gain versus frequency, is designed to discriminate against low frequency signals and in particular the interference, 60 Hz and artifact noises and at the same time to provide significant gain, e.g., 5, to those signals having higher frequency components, i.e., the leading and trailing edge components. In particular, signals with frequencies from zero to 460 Hz are amplified with a substantially unity gain, with the gain increasing as the signal frequency increases to 2300 Hz, at which point an illustrative gain of 5 is imparted to the input signals. The ultimate gain is limited by the expression shown in FIG. 7 to prevent saturation of the amplifier to low signal levels, which would otherwise change the transfer response of the circuit. The circuit 32 may be theoretically modeled as shown in FIG. 8, wherein the various input and output voltages are expressed as follows:

$$\frac{V_p e^{-t/T1}}{T_2} = \frac{V_c}{T_2} + \frac{dV_c}{dt} \quad (1)$$

$$e^{t/T2} V_c = \int_0^t \frac{(V_p e^{-\mu T})}{T_2} e^{\mu/T2} d\mu + C \quad (2)$$

$$= \int_0^t \frac{V_p e^{\mu(1/T2 - 1/T1)}}{T_2} d\mu + C$$

$$V_c = \frac{V_p [e^{-t/T1} - e^{-t/T2}]}{T_2(1/T_2 - 1/T_1)} \quad (3)$$

$$V_o = \frac{(V_{in} - V_c) R_F}{R_s} = \quad (4)$$

$$\frac{R_f}{R_s} \left[ V_p e^{-t/T1} - \frac{V_p (e^{-t/T1} - e^{-t/T2})}{(1 - T2/T1)} \right]$$

Use max min to find overshoot $$\frac{dV_o(t_{max})}{dt} = 0 \longrightarrow t_{max} = \frac{2\ln T2/T1}{(1/T_1 - 1/T_2)} \quad (5)$$

The time constant of the circuit 32 is critically selected such that it is short enough to allow the amplifier to recover from the detection of the leading edge sufficiently to detect the start of the trailing edge with specified confidence. This is illustrated in FIG. 8, wherein for a good response of the wave shaping amplifier 32, a recovery of approximately 95% has been obtained within a period of $t_{min}$ or 200 microseconds. Thus, the value of $\tau_{2max}$ may be calculated as follows:

$$Y_{2max} = (200 \times a^{-6}/- 1n0.5) = 67 \ \mu s \quad (6)$$

On the other hand, the circuit 32 cannot respond too fast or it will not generate sufficient output for a slow-trailing edge. To detect the trailing edge of the pacer pulse, the time constants are calculated to ensure decay of the output of the circuit 32 in 200 $\mu s$ $Y_1 = 67 \ \mu s$, as follows:

$$V_{in} = V_p(1 - e^{-t/Y1}) Y_1 = 67 \ \mu s$$

Applying the same technique used earlier:

$$V_o = \frac{T_2 [e^{-t/T1} - e^{-t/T2}]}{T_1 - T_2}$$

$$t_{max} = \frac{T_2 T_1}{T_2 - T_1} \ln \frac{T_2}{T_1}$$

$V_{omax}$ = undefined for $T_1 = T_2$
= $0.274 V_p$ at $t_{max} = 50.5 \mu s$ (65 × $V_{omax}$ × 1mv = 17.8mv)
= $0.32 V_p$ at $t_{max} = 57.6 \mu s$ (2 × $V_{omax}$ × 1mv = 20.8mv)

The preceding analysis indicates that $Y_2 = 67 \ \mu s$ is clearly the optimum amplifier time constant given the worst case.

The above analysis can be visualized in FIG. 4B which shows the output of the differentiator or wave shaping amplifier 32. It is contemplated that if a typical differentiator circuit as suggested by the prior art was used, that the sloping or drooping wave form of a degraded pulse might cause its output to overshoot as at time t4. If the negative going amplitude at time t4, as shown in FIG. 4B, is of sufficient amplitude it may well serve to trigger prematurely the pulse width detector 51. However, the transfer characteristic of the wave shaping amplifier 32 has been selected so as to reduce the amount of overshoot potentially occurring a time t4 and to provide a shelf appearing between times t4 and t5 of sufficient amplitude to bring up the potential overshoot and thus prevent premature detection of the trailing edge.

As seen in FIG. 3, the output of the wave shaping amplifier 32 is applied to one input, while the cardiac activity signals including the pacer pulse and other noise are applied to a second input of the differential amplifier 34. Essentially the differential amplifer 34 subtracts the output of the amplifier 32 from the amplifier activity signals and will provide a difference output as shown in FIG. 4C. In general terms, the differential amplifier eliminates the shelf occurring between times t4 and t5 which is not needed for the detection of the leading edge in that the rise time is sufficiently high, i.e., the frequency components are sufficiently high, so that the amplifier 32 amplifies with sufficient gain these components to provide an accurate indication of the occurrence of the leading edge. As explained above, the output of the differential amplifier 34 is applied to the leading edge detector 36 which provides outputs indicative of the occurrence of positive and negative going leading edges upon its line D and E, respectively.

Further, the output of the differential circuit 32 is applied to the limiter 48 which acts as an amplifier. The limiter 48 and the pulse width detector 51 function to detect the trailing edge; as shown in FIG. 4A, the fall time of the trailing edge is not as steep as the rise time of the leading edge. Thus, the frequency components of the trailing edge are less than those of the leading edge and the wave shaping amplifier 32 does not provide as much gain to the signals corresponding to the trailing edge as to the leading edge signals. Thus, the limiter amplifier 48 provides further gain for the trailing edge signals so as to actuate the pulse width detector 51 and in particular to provide a signal thereto that will exceed the threshold level for either positive or negative signals to provide corresponding outputs upon its lines F and G respectively. Thus from the foregoing explanation, it is seen that the threshold levels of the pulse width detector 51, the gain of the limiter 48, as well as the time constant of the wave shaping amplifier 32 are selected so that a defined indication is provided upon the output lines F and G of the pulse width detector corresponding to the occurrence of the trailing edges of the pacer pulses.

Vcc Regulator 28

The regulator 28 is a feedback amplifier known in the art as a Brokaw reference. The feed forward amplifier comprises transistors Q48, Q49, Q45, Q46. The feedback network is comprised of transistor Q44, diode CR2, and resistors R29 and R30. At equilibrium, the current flowing through resistor R31 is due to area scaling in the amplifier transistors Q48-Q49, Q45-Q46 which holds a voltage equal to KT/q in pin 8 across resistor R31. The emitter currents from the transistors Q48 and Q49 sum to develop a voltage across resistor R32, which when added to the base-emitter voltage of transistor Q48 will equal 1.25 V.

The feedback network comprised of resistors R29 and R30, multiplies the voltage at the base of transistor Q48 to 5 V at the cathode of diode. Diode tends to compensate for the base-emitter drop of transistor Q43, whose emitter potential is used as the Vcc power line for the rest of the chip.

Since there is a possibility that the regulator 28 will not "start" by itself, a start-up circuit is provided by resistor R35, diode CR3 and transistor Q50. When voltage is applied across resistor R35, diode D3 will bias transistor Q50 so that its collector will inject current into the current mirror transistors Q46 and Q45. Transistor Q44 will then provide current gain and pull the base of transistor Q48 to its quiescent potential. At this time the voltage across resistor R32 is large enough to cut off transistor R50 so that it does not impair regulator operation.

Transmission Timer 30

The timer action is formed by an external capacitor to ground from Pad 2 and resistor R37. When the start switch is closed, the capacitor is charged to the battery potential and current is developed through resistor R37 to an NPN current mirror transistors Q60, Q59 and Q58. This mirror supplies bias current to a comparator formed by transistors Q53 to Q59, and the current through transistor Q58 will pull the base of transistor Q56 to an above-ground by developing a voltage drop across resistor R36 which is equal to resistor R37. The base of transistor Q57 is held at or below B+ voltage by diode CR6 so that the comparator is "on" and transistor Q53 is saturated. Transistor Q53 supplies current to the open loop amplifier formed by transistors Q52 and Q51. When transistor Q55 is on, transistor Q51 is saturated also and supplies B+ potential to the Vcc regulator 28 which powers the reset of the chip.

When the start switch is released, the capacitor discharges through diode CR6, resistor R37 and transistor Q60 so that the current through resistor R37 decreases exponentially. This causes the base of transistor Q56 to rise as the base of transistor Q57 decreases in potential. The comparator switches off when the two bases equal each other at B+/2. Transistor Q53 is then cut off, which in turn shuts down the drive to the other circuits. The external capacitor continues to discharge until depleted.

Note that diode CR5 is used to compensate for the voltage drops of transistor Q60 and diode CR6 so that the expression for the timer interval is: T=R37C ln2 which is independent of the voltage B+.

Input Amplifier 12

The input amplifier 12 is comprised of two amplifiers, an input differential amplifier and a driven lead amplifier. The differential amplifier is a standard configuration, i.e., transistors Q1 and Q2 are the differential pair, resistors R1 and R2 are emitter feedback resistors to set the gain against the load resistor R3. A 6.25 $\mu$a bias current is provided through the collector current of transistor Q11, part of an NPN current rail set up by transistors Q8 and Q9. The rail receives current via a PNP current mirror, transistors Q13-Q14, which is sourced from a Brokaw reference similar to that discussed previously. The 1.25 reference voltage at the emitter of transistor Q27 develops a 6.25 $\mu$a current through resistor R13 which is routed to the PNP mirror via transistor's Q27 collector.

The load resistor R3 develops 1 vdc across it. Transistors Q37 and Q33 form a darlington amplifier to buffer the load resistor R3 from the rest of the circuitry. Therefore, the output potential of the buffer amp is approximately Vcc−2.35 v=Vcc/2.

The driven lead amplifier is an open loop operational amplifier. Transistors Q3 and Q4 form a differential pair fed by transistor Q10. A current source load is formed by transistors Q5 and Q6, fed by transistor Q3B, with one of transistor's Q5 collectors providing bias to transistor Q3C which performs the action of reducing the input bias current as well as compensating for the base-emitter drop of transistors Q1 and Q2. Transistor Q7 provides a second stage of gain into the current source load of transistor Q12. The operational amplifier compares the common mode signal available at the collector of transistor Q11, to a dc bias potential (Vcc/2 provided by resistors R12 and R12A). If a difference exists, the output of the driven lead amplifier will remove the common mode signal by applying a potential to Pin 17 which, when added to the common mode signal, produces the desired dc potential a the collector of transistor Q11.

Capacitor Bias Amplifier 25

The amplifier 25 supplies a low impedance potential, referenced from Vcc, on Pin 16 equal to the potential developed on Pin 15 when Pins 17, 18 and 1 are shorted together. This will keep the leakage current across the low frequency cutoff capacitor, connected between Pins 15 and 16, as low as possible and also provide supply ripple rejection when capacitors are used in subsequent circuits where load resistors are referenced to Vcc also.

The amplifier 25 accomplishes its function by setting up a potential across resistor R114 equal to that across resistor R3. This is done by deriving a current through transistor Q40 from the same rail as in sourcing current to resistor R3 through transistor Q11. Since the differential pair delivers only half of the current available from transistor Q11 to resistor R3, resistor R114 is made equal to half of resistor R3. A buffer amplifier comprising transistors Q34 and Q35 is provided to simulate the voltage drop due to transistors Q32 and Q33. A unity gain operational amplifier comprised of transistors Q36-Q39, Q41-Q42, is employed to reduce the output impedance below 1Ω.

ECG Amplifier 22

The ECG amplifier 22 includes a differential transconductance amplifier comprised of transistors Q61-Q66, and an associated current bias circuit comprised of transistors Q67-Q73.

Bias current is derived by setting the base-emitter drop of transistor Q70 across an external resistor at PAD 7 to ground. The current through this resistor becomes the collector current of transistor Q71 and then reflected by the current mirror transistors Q73-Q72 into the collector of transistor Q70 and the base of transistor Q71. Transistor Q71 monitors the current of transistor's Q70 collector and provides feedback gain to maintain the quiescent value. Resistor R150 is used to start the circuit when power is applied. The 5 pf capacitor C2 insures stability of the feedback network.

Transistors Q67-Q69 form a current mirror rail to provide current drain in integer multiples of transistor's Q70 collector current. Transistor Q67 provides current to the differential connected pair of transistors Q61-Q62 and its active load comprised of transistors Q64, Q63 and Q66. The output of the differential amplifier (the collectors of transistors Q62 and Q63) is in the form of an additive or subtractive current, proportional to the input voltage, summed with collector bias current of transistor Q68. The resultant current is routed through the CCO control circuit 16 (cathodes of diode D8) along with the collector current of transistor Q69.

The other output of the EKG amplifier 22, i.e., the collector of Q65, is made available at Pad 9. A voltage gain of 35 and 1 vdc is obtained across a 500 KΩ resistor connected from Pad 9 to ground. This output can be used as a general EKG signal with a high-pass frequency response equal to that transmitted by the CCO 16.

CCO Control 24

The CCO control 24 is a differential comparator comprised of transistors Q75-Q78 that selects which of the two current drives, ECG amplifier 22 or the collector current of transistor Q69 is used to drive the CCO 16 while the current that is not used is shunted away from the CCO input. Pad 8 controls the state of this comparator. If 8 is pulled below 1 V, diodes CR10 and CR10a will pull the base of transistor Q76 below the 2.5V potential on transistor Q75 set by resistors R48 and R49 from Vcc, turning transistors Q76, Q77 and Q75 off, and saturating transistor Q78. All of the collector current of Q69 then flows through transistor Q78 since diode CR8 prevents current flow to transistor Q79, the CCO input, while permitting the ECG output current to flow through the other emitter of diode CR8 to transistor Q79. Therefore, the ECG amplifier ouput controls the CCO 16 when Pad 8 is low.

When Pad 8 is allowed to float, or is taken to B+, diodes CR10 and CR10a reverse bias and allow resistor R33 to pull the base of transistor Q76 to Vcc, turning transistor Q76 on and saturating transistor Q77. This shunts the ECG output current through transistor Q77 and allows the collector current of transistor Q69 to set the CCO frequency.

Current Controlled Oscillator (CCO) 16

The CCO 16 operates on the principle of a controlled +I current source charging a capacitor between high- and low-voltage limits. A Schmidt trigger monitors the capacitor voltage and switches the direction of the charging current when the capacitor voltage equals either of the voltage limits. Therefore, the capacitor voltage oscillates as a trinagular waveform between the specified limits. The Schmidt trigger output is buffered and used as the CCO output at Pad 4.

The input device to the CCO 16 is transistor Q79, which sets up a current bias rail comprised of transistors Q80-Q85. The rail is used to supply current to the Schmidt trigger as well as the +I current source. The +I source is formed by the collectors of transistor Q81 and Q92. Transistor Q92 supplies twice the current as transistor Q81 or Q80 due to mirror action against transistor Q93. The output of the Schmidt trigger is the emitter of transistor Q89. It controls the direction of current into Pad 6 by controlling the emitter potential of transistor Q92.

The Schmidt trigger comprises a differential pair of transistors Q87 and Q81, feedback current mirror including transistors Q90-Q91, current load 83, and output buffer device Q89. Transistors Q84-Q85, Q94-Q97 are used as clamps to set the trip points for the Schmidt trigger. In operation, the base of transistor Q87 is the input of the differential pair that monitors the capacitor voltage. The current mirror of transistors Q90-Q91 connects to the base of transistor Q88 in a positive feedback arrangement. The collector current of transistor Q83 acts to pull up the bases of transistors Q89 and Q88, when transistor Q91 turns off. The emitters of transistors Q94-Q95 are set to clamp the voltage on the bases of transistors Q88 and Q89 between $\phi 97$ and $\phi 95$ and $\phi 97 + \phi 96 - \phi 94$ (this translates to a voltage swing equal to $\phi 94$ on the base of transistor Q88 as well as the capacitor as a consequence). Therefore, the transistor's Q89 emitter will travel between ground and one $\phi$, either cutting off the current in transistor Q92 or allowing it to produce twice the current available from transistor Q80.

The collector current available from transistor Q87 oscillates at the capacitor's frequency. Transistors Q101 and Q74 provide current gain, and diodes CR11 and CR12 are used to level shift the output to compensate for the output darlington connected at Pad 4. Voltage swing is set by using transistor Q98 to develop a current through resistor R36, reflecting it through transistors Q99-Q100, which then causes a 2.5 V voltage drop across resistor R58 when transistor Q101 is cut off.

CCO Low Voltage Inhibit 26

The inhibit circuit 26 is designed to stop the CCO input when the B+ voltage drops below a predetermined level. Transistors Q17 and Q16 form a differential pair with active load comprised of transistors Q21-Q20. The 1.25 V Brokaw reference output, i.e., transistor's Q27 emitter, provides a stable supply and temperature independent voltage reference to the base of transistor Q17. A resistor comprised of resistors R8 and R9 provides B+/5.5 to the base transistor Q16, since transistor Q81 is saturated during operation. One μ a bias to the differential pair is supplied by transistor Q22 from the rail of transistors Q22-Q26, set up by the Brokaw reference.

When B+ falls below 6.87 V, the base of transistor Q16 will be below the base of transistor Q19. Q19 will saturate, cutting off bias current from Q82 to the CCO comparator and stopping the CCO output at a high potential. Transistor Q18 provides positive feedback to the base of transistor Q16 pulling it down another 40 mv. This action requires the B+ voltage to increase 220 mv before the comparator reverses its state and allows the CCO 16 to resume.

Differentiator 32

The differentiator 32 is a non-inverting operational amplifier including resistors R60 and R61 and an external capacitor C to provide a frequency rsponse of the form:

$$T(s) = \frac{(R61 + R60)C + 1}{SCR61 + 1}$$

Primary requirements of this operational amplifier are low input offset voltage, a voltage swing from near Vcc to near ground, and large open loop gain. Offset conditions are minimized by closely matching the bias currents which feed the differential pair of transistors Q102-Q103, and a current source load including transistors Q104-Q105. Transistors Q102-Q103 are circular emitter geometry devices to optimized mismatch. Transistor Q159 tracks the variations in input potential applied to the differential pair so that current cancellation to the base of transistor Q106 is unaffected by common mode effects. Resistor R59 compensates for the input bias offset developed across resistor R60.

A second stage of gain is provided by transistor Q106 which can saturate to Vcc if required. Capacitor C3 is used to compensate the amplifier by placing a dominant pole in the open loop gain.

Bias current is generated from resistor R65 into a current rail including transistors Q114-Q112. Transistor Q115 supplies the active load; transistor Q113 supplies the differential pair, and transistor Q112 is an active pulldown load for transistor Q106.

Differential Amplifier 34

The differential amplifier 34 comprising transistors Q107-Q108 is used to modify the response of the differentiator 32 by being connected across input to output. The differential amplifier 34 nullifies the dc gain of the second differentiator 32 so that the first differential amplifier 34 response is of the form (across resistor R66):

$$J(s) = \frac{As(R61 + R60)C}{SCR61 + 1}$$

where $A = (R66/4R20) \ln 8$

The gain, A, is a result of the current developed by a Brokaw reference, comprised of transistors Q23-Q30, routed into the emitters of transistors Q107-Q108 via a current rail formed by transistors Q116-Q119. The current produces a transconductance through transistors Q107-Q108 and a gain and bias voltage across resistor R66 of 150 mv. Therefore, the output signal swing is limited to +150 mv.

The amplifier output is darlington buffered to drive the leading edge detector 36.

Limiter 48

The limiter 48 performs the same basic function as the differential amplifier 34 (gain and limiting) without altering the transfer function established by the differentiator 32. Transistors Q130-Q131 form a differential pair similar to transistors Q107-Q108 but its inputs are connected to the output of the differentiator and the roll-off capacitor at Pad 15. Pad 15 provides an effective ac ground to the differential amplifier input so that the output (voltage across resistor R87) is essentially amplified differentiator signals.

Since this limiter 48 is fed from the same current rail as the first differential amplifier 34 previously discussed, the gain is of the same form:

$A = (R87/4R20) \ln 8$ $$T(s) = \frac{As(R61 + R60)C + 1}{SCR61 + 1}$$

The limiting voltage swing at the output resistor R87, is approximately 400 mv.

Transistors Q136 and Q134 are used to cancel the input bias current effects, due to transistor Q130, on the ECG amplifier inputs through resistors R23 and R22. The single-ended limiters output is darlington buffered by transistors Q132-Q133, to drive the PW detector 51.

Leading Edge Detector 36

The leading edge detector 36 is simply two threshold comparators operating in parallel. One comparator responds to a +18 mv level and the other comparator responds to a −18 mv level. These outputs are applied to the leading edge flip-flop 44 as well as being ORed and used to trigger a monostable multivibrator, or one-shot 42. The one shot 42 in turn disables the detector outputs. (This is definitely a race condition but there is enough delay involved to accomplish the setting or resetting of the flip-flop 44 before the impulse is removed.) By disabling the detector 36, no more edges can set the flip-flop 44 until the one shot 42 has cycled.

Both comparators are completely symmetrical so it is necessary to explain the operation of only one. The positive threshold comparator is composed of transistors Q120, Q121, Q124-Q126 and Q173. Transistor Q118 feeds a 6 μ a bias current, from the Brokaw reference discussed earlier, to the differential paired transistors Q121-Q120. Transistor Q120 is a device fabricated with twice the emitter area as Q121 so that in order to make the two collector currents match, the base of transistor Q121 must be raised 18 mv above the base of transistor Q120. Transistors Q124-Q126 are just a current mirror configuration so that current is switched to or from the base of transistor Q173.

In operation Pad 11 is bypassed rather heavily to Pad 16 so it can be assumed to be a constant dc potential. When the differentiator 32 responds to a positive leading edge, the differential or amplifier 34 responds also and the potential at the emitter of transistor Q111 increases. The base of transistor Q121 is not bypassed and, therefore, will follow transistor Q111's emitter exactly (resistor R74 matches resistor R75 to compensate for input bias offset. Resistor R75 and external capacitor C bypass Pad 11). When +18 mv is exceeded, transistor's Q121 collector current will exceed transistor's Q124 collector current and current will start to flow out of the base of transistor Q173. Transistor Q173 correspondingly adds gain to the current mismatch which is then used to set the flip-flop 44 and trigger the one shot 42.

Pulse Width Detector 51

The pulse width detector 51 is exactly the same configuration as the leading edge detector 36. The basic difference between the two detectors is that the one shot 42 disables the outputs of the leading edge detector 36, while it enables the outputs of the pulse width detector 51 allowing them to set or reset the pulse width flip-flop 54 depending on the polarity of the edges of the artifact or pacer pulse.

One Shot 42

The one-shot 42 is a low gain operational amplifier comprised of transistors Q150–Q154, with positive feedback to the base of transistor Q153 and RC timing provided by eternal components connected from Pad 13 to ground. The operation of the one shot 42 is more easily understood by following it through one of its cycles. In its quiescent state, the circuit is "latched" with transistors Q150 and Q153 both saturated. The base of transistor Q153 is within a saturation voltage (?) of Vcc, and transistor Q155 is holding Pad 13 at a $V_{be}$ below transistor's Q153 base potential. This insures that transistor Q154 is cut off and also that transistor Q152, the active load, is not drawing current from transistor's Q150 base and the circuit remains latched.

The cycle is started when the one shot 42 is triggered by transistor Q156 via the OR'ed output of transistors Q173A and Q123A from the leading edge detector 36. Transistor's Q156 collector pulls the base of transistor Q153 below the base of transistor Q154, which is held at its potential by the external RC circuit at Pad 13. Thus transistor Q153 is cut off and transistor Q154 is turned on activating transistors Q151 and Q152. The two collectors of transistor Q151 pull current away from the bases of transistors Q123 and Q173, thereby disabling the leading edge detector 76. Meanwhile, transistor Q152 pulls current away from the base of transistor Q150 cutting it off. This allows the potential on the base of transistor Q153 to be set, by the voltage divider comprised of resistors R96, R97, CR13, CR14 at a $\phi$ below Vcc/2. Transistor Q149 is also cut off with transistor Q150 enabling transistors Q147 and Q148, the outputs of the pulse width detector 51. Now since transistor Q155 is reverse biased, there is nothing to hold the potential at transistor's Q154 base so the external components will discharge until the potential at the bases of transistors Q153 and Q154 are equal.

When the base potential of transistor Q154 drops below that of transistor Q153, the collector currents imbalance at the base of transistor Q150 allowing positive feedback to take over and "latch" the one shot 42 into its quiescent condition. In the latched mode, the leading edge detector outputs are enabled and the pulse width detector outputs are disabled.

Leading Edge Flip-Flop 44

The flip-flop 44 is a simple R-S type, Eckles-Jordan saturating configuration with two inverters connected across each other. Transistors Q157–Q158 form the inverters with device CR15 and transistor Q174 clamping the output swing so that bias current is always supplied to the pulse width flip-flop's transistors, Q167–Q168, described below.

The leading edge flop 44 is set and reset by the collectors of transistors Q173A and Q123A respectively by pulling a current from the base of the transistor desired to be saturated. The saturated transistor then cuts off the remaining device by shunting current away from its base via the saturated collector. The saturated device remains so after the set current is withdrawn because the cut-off device is no longer shunting current away from its base.

The outputs of the flip-flop 44 are routed through resistors R79 and R104 to the bases of transistors Q171, Q172 respectively, i.e., the inputs to the exclusive-OR gate 46.

Pulse Width Flip-Flop 54

This is the dual of the leading edge flop 44. Instead of using split collector PNP transistors, two NPN devices are operated in parallel with 100 KΩ base degeneration to avoid current hogging problems. Output clamps are not necessary on the flip-flop 42 since the NPN betas are higher so set current margins are larger as well. The pulse width flip-flop 54 is set and reset by transistors Q165 and Q164 respectively acting as inverter/drivers from the outputs of the pulse width detector 51.

Exclusive-OR Gate 46

The exclusive-OR gate 46 is simply two NPN transistors Q171–Q172 with both collectors connected to the pulse width output, Pad 14. The outputs of the leading edge flip-flop 44 provide base current to either transistor Q171 or Q172, depending on the polarity of the pulse, but not both. The outputs of the pulse width flip-flop 54 then control the current into the bases of transistors Q171 and Q172 also but function only as shunt switches. The function performed by the exclusive-or 46 is then:

PW Out=(QLE AND QPW) OR (QLE AND QPW)

Note that the polarity of the pulse width flip-flop output is reversed if the polarity of the leading edge is negative. This acts to keep the polarity of the pulse at Pad 14 positive irrespective of the input pulse polarity.

Numerous changes may be made in the above-identified apparatus and the different embodiments of the invention may be made without departing from the spirit thereof; therefore, it is intended that all matter contained in the foregoing description and in the accompanying drawings shall be interpreted as illustrative and not in a limiting sense.

I claim:

1. Apparatus for accurately detecting the pulse width of simulating pulses applied by an artificial pacemaker to a patient's heart, each of the stimulating pulses comprising a relatively fast rising leading edge followed by an attenuated wave form portion and terminating in a relatively slow falling trailing edge, said apparatus comprising:

wave shaping amplifier means for receiving and amplifying the stimulating pulses along with low frequency noise signals in accordance with a transfer function such that low frequency component signals are amplified with a relatively low gain and higher frequency component signals are amplified with a relatively high gain whereby said noise signals are substantially discriminated against;

first normally deactuated threshold means responsive to the output of said amplifier means of an amplitude greater than a first predetermined level for providing a first output signal indicative of the occurrence of the trailing edge;

differential amplifier means responsive to the output of said amplifier means and to the stimulating pulses and noise signals, for providing a difference output signal corresponding to the difference between the input signals;

second normally actuated threshold means responsive to the difference output of an amplitude greater than a second predetermined level for providing a second output signal indicative of the occurrence of the leading edge;

said transfer function of said amplifier means and said first predetermined level being selected to provide an accurate indication of the occurrence of the trailing edge without prematurely responding to the attenuated wave form portion of the stimulating pulse; and means responsive to the second output signal for disabling said second threshold means and for enabling said first threshold means to initiate detection of the trailing edge of the stimulating pulse.

2. Apparatus as claimed in claim 1, wherein said first threshold means is responsive to a wave shaping amplifier output of an amplitude greater than the first predetermined level and of a first polarity to provide the first output signal and to a wave shaping amplifier output of an amplitude greater than the first predetermined level and of a second polarity opposite to the first polarity for providing a third output signal, said second threshold means responsive to a differential amplifier output of an amplitude greater than the second predetermined level and of the first polarity for providing the second output signal and to a differential amplifier output of an amplitude greater than the second predetermined level and of the second polarity for providing a fourth output signal.

3. Apparatus as claimed in claim 2, wherein there is further included logic means responsive to the second output signal and the subsequent first output signal to provide a pulse-like signal having a leading and trailing edge accurately corresponding to the leading and trailing edges of the stimulating pulse.

4. Apparatus as claimed in claim 3, wherein said logic means comprises a first flip-flop coupled to said second threshold means and set in response to the second output signal to provide a first high going logic signal and reset in response to said fourth output signal to provide a first low going output logic signal, and a second flip flop coupled to said first threshold means and reset in response to said first output signal to provide a second low going output logic signal and set in response to the third output signal to provide a second high going output logic signal.

5. Apparatus as claimed in claim 4, wherein said logic means comprises an exlcusive NOR gate responsive to the first and second logic output signals to provide a pulse like output signal whose leading and trailing edges correspond respectively to the leading and trailing edges of the stimulating pulse.

6. Apparatus as claimed in claim 2, wherein there is further included logic means responsive to the fourth output signal and the subsequent third output signal to provide a pulse-like signal having a leading and trailing edge accurately corresponding to the leading and trailing edges of the stimulating pulse.

7. Apparatus as claimed in claim 1, wherein said wave shaping amplifier means has a time constant set sufficiently high to provide the first output signal with an amplitude greater than the second predetermined level and sufficiently low to reject undesired low frequency noise.

8. Apparatus as claimed in claim 7, wherein there is further included amplifier means for amplifying and applying the shaping amplifier output to said first threshold means.

9. Apparatus as claimed in claim 8, wherein said amplifier means has a selected gain, said gain of said amplifier means, said first predetermined level and said time constant of said wave shaping amplifier means selected so that said first threshold means provides an output indicating the occurrence of the attenuated trailing edge of a stimulating pulse.

10. Apparatus for accurately detecting the relatively sharp leading edge and attenuated trailing edge of stimulating pulses applied by an artifical pacemaker to a patient's heart and for transmitting the detected stimulating pulses, combined with cardiac signals of a patient's heart, over a limited bandwidth medium to a remote station, said apparatus comprising:

(a) selectively actuatable modulation means for generating a carrier signal of a frequency suitable to be transmitted over the limited bandwith medium;

(b) detection means for accurately detecting the pulse width of stimulating pulses applied by an artificial pacemaker to a patient's heart, each of the stimulating pulses comprising a relatively the fast rising leading edge followed by an attenuated wave form portion and terminating in the relatively slow falling trailing edge, said detector means comprising:

(1) wave shaping amplifier means for receiving and amplifying the stimulating pulses along with low frequency noise signals in accordance with a transfer function such that low frequency component signals are amplified with a relatively low gain and higher frequency component signals are amplified with a relatively high gain such that said noise signals are substantially discriminated against;

(2) first normally deactuated threshold means responsive to the output of said amplifier means of an amplitude greater than a first predetermined level for providing a first output signal indicative of the occurrence of the trailing edge;

(3) differential amplifier means responsive to the output of said amplifier means and to the stimulating pulses and noise signals, for providing a difference output signal corresponding to the difference between the input signals;

(4) second normally actuated threshold means responsive to the difference output of an amplitude greater than a second predetermined level for providing a second output signal indicative of the occurrence of the leading edge;

(5) said transfer function of said amplifier means and said first predetermined level being selected to provide an accurate indication of the occurrence of the trailing edge without prematurely responding to the attenuated wave form portion of the stimulating pulse; and (6) means responsive to the second output signal for disabling said second threshold means and for enabling said first threshold means to initiate detection of the trailing edge of the stimulating pulse; and (c) means responsive to the first and second output signals for providing a pulse like signal having a pulse width expanded with respect to the period between the first and second output signals and applying the pulse like signal to actuate said modulation means to transmit the carrier signal over the limited bandwidth medium for the expanded pulse width.

11. Apparatus for accurately detecting the pulse width of stimulating pulses applied by an artificial pacemaker to a patient's heart, each of the stimulating pulses including a relatively fast rising leading edge, a relatively slow falling trailing edge and an attentuated, sloping portion therebetween, said apparatus comprising:

(a) first detection means coupled to receive the stimulating pulses along with noise signals for detecting the leading edge of each of the stimulating pulses and for providing a first output indicative of the occurrence thereof; and (b) second detector means actuatable after the detection of the leading edge for detecting the trailing edge of each stimulating pulse and coupled to receive and variably amplify each of the stimulating pulses in accordance with a transfer function such that said second detector means provides a second output signal indicative the occurrence of the trailing edge without prematurely responding to the attenuated, sloping portion to provide a false indication of the occurrence of the trailing edge.

* * * * *

UNITED STATES PATENT AND TRADEMARK OFFICE
CERTIFICATE OF CORRECTION

PATENT NO. : 4,226,245
DATED : October 7, 1980
INVENTOR(S) : Robert M. Bennett

It is certified that error appears in the above-identified patent and that said Letters Patent are hereby corrected as shown below:

Col. 20, line 48, "simulating" should be --stimulating--.

Col. 23, line 8, "attentuated" should be --attenuated--.

Signed and Sealed this

Ninth Day of December 1980

[SEAL]

*Attest:*

SIDNEY A. DIAMOND

*Attesting Officer*   *Commissioner of Patents and Trademarks*